United States Patent
Bucka et al.

(10) Patent No.: US 6,815,545 B2
(45) Date of Patent: Nov. 9, 2004

(54) METHOD FOR PRODUCING MELAMINE

(75) Inventors: Hartmut Bucka, Eggendorf (AT); Gerhard Coufal, Leonding (AT); Ferdinand Koglgruber, Linz (AT)

(73) Assignee: Agrolinz Melamin GmbH, Linz (AT)

(*) Notice: Subject to any disclaimer, the term of this patent is extended or adjusted under 35 U.S.C. 154(b) by 0 days.

(21) Appl. No.: 10/399,637

(22) PCT Filed: Oct. 15, 2001

(86) PCT No.: PCT/EP01/11890
§ 371 (c)(1), (2), (4) Date: Oct. 7, 2003

(87) PCT Pub. No.: WO02/34730
PCT Pub. Date: May 2, 2002

(65) Prior Publication Data
US 2004/0054175 A1 Mar. 18, 2004

(30) Foreign Application Priority Data
Oct. 20, 2000 (AT) .......................................... 1802-2000

(51) Int. Cl.$^7$ ............................................ C07D 251/60
(52) U.S. Cl. ...................................... 544/201; 544/203
(58) Field of Search ................................. 544/201, 203

(56) References Cited
U.S. PATENT DOCUMENTS
3,116,294 A  12/1963  Marullo et al.

FOREIGN PATENT DOCUMENTS

| DE | 1 228 266 A1 | 11/1966 |
| EP | 0 612 560 A1 | 8/1994 |
| EP | 0 808 836 A1 | 11/1997 |
| WO | WO 95/01345 | 1/1995 |
| WO | WO 99/00374 | 1/1999 |

OTHER PUBLICATIONS

International Search Report of corresponding International application No. PCT/EP/01/11890, dated Feb. 19, 2002.

International Preliminary Examination Report of corresponding International application No. PCT/EP/01/11890, dated Apr. 17, 2002, with English translation.

*Primary Examiner*—Peter O'Sullivan
(74) *Attorney, Agent, or Firm*—Christie, Parker & Hale, LLP

(57) ABSTRACT

A process for the production of melamine by pyrolysis of urea in a high-pressure reactor having a vertical central pipe is provided. The melamine flows upwards into the reactor from below, mixes in the lower part of the reactor with a urea melt, and optionally NH$_3$, introduced into the reactor from below, and emerges from the central pipe in the upper part of the central pipe. Part of the melamine formed flows downward in the annular space between the central pipe and reactor wall, and the remainder is expelled for further work-up. The off-gases are removed at the top of the reactor. A reactor for carrying out the process is also provided.

6 Claims, 1 Drawing Sheet

METHOD FOR PRODUCING MELAMINE

CROSS-REFERENCE TO RELATED APPLICATION

This application is a National Phase Patent Application of International Application No. PCT/EP01/11890, filed on Oct. 15, 2001, which claims priority of Austrian Patent Application Number A 1802/2000, filed Oct. 20, 2000.

FIELD OF THE INVENTION

The invention relates to a process and a device for the production of melamine by pyrolysis of urea.

BACKGROUND OF THE INVENTION

In the high-pressure processes for the production of melamine, urea is reacted to give melamine by means of an endothermic liquid-phase reaction. The liquid melamine, depending on the pressure and temperature conditions in the reactor, additionally contains different amounts of dissolved $NH_3$ and $CO_2$, and condensation by-products and unreacted urea. The melamine thus obtained is then solidified, for example, by quenching with water or with ammonia, by sublimation with subsequent desublimation or by releasing the pressure under specific conditions.

The reactor used is customarily a tank reactor with a central pipe and heating elements arranged outside the central pipe, which provide the heat necessary for the reaction. These heating elements are pipe bundles, in which a salt melt circulates, arranged parallel to the central pipe. Urea and $NH_3$ are introduced at the bottom of the reactor, impinge on a distributor plate which is located underneath the central pipe and react in the free space between the pipe bundles, in which melamine is already situated, with decomposition and evolution of gas to give melamine. In WO 99/00374, such a reactor is depicted schematically, the flow direction of the melt also being indicated such that the reaction mixture outside the central pipe flows upwards between the pipe bundles and separates there into off-gas and liquid melamine. The off-gas is removed at the top of the reactor, one part of the melamine melt is removed from the reactor via an overflow and the other part of the melamine melt flows downwards within the central pipe on account of gravity.

This previously used type of reactor, however, has the disadvantage that the pipe bundles, in particular in the case of relatively high urea throughputs, corrode relatively rapidly and therefore have to be frequently exchanged.

SUMMARY OF THE INVENTION

Unexpectedly, it has now been found that the corrosion rate of the salt melt pipes can be significantly lowered if the mixture of urea with melamine and its decomposition takes place not outside, but inside the central pipe. Contrary to the original assumption that the flow direction of the melamine melt is such as indicated in WO 99/00374, it has been found that the flow direction of the melamine melt in the arrangement according to the invention is exactly the reverse, the melt in fact flows upward within the central pipe and downward outside the central pipe.

The supply of heat necessary for the overall endothermic reaction takes place by means of the heating pipes arranged outside the central pipe during the movement of the melt downward, so that in the lower part of the reactor an approximately 3–30° C., preferably 5–15° C., higher temperature prevails than in the upper part. The fact that the melamine melt in the upper part of the reactor, where it is removed via an overflow, is colder than in the lower part means a further advantage compared with the arrangement according to WO 99/00374, since the melamine melt in the subsequent sections has to be cooled less, and the equilibrium position of the melt at the lower temperature is shifted in the direction of the melamine, so that fewer by-products are formed.

The invention accordingly relates to a process for the production of melamine by pyrolysis of urea in a high-pressure reactor having a vertical central pipe with formation of a melamine melt, which is characterized in that the melamine melt circulating in the reactor mixes in the lower region of the reactor with a urea melt introduced into the reactor from below and optionally introduced $NH_3$, the reaction mixture formed, consisting essentially of melamine, $NH_3$, $CO_2$ and optionally reaction intermediates, flows upwards from below in the central pipe, the reaction mixture formed emerges from the central pipe in the upper part of the central pipe, the separation between melamine and off-gas takes place at the top of the reactor above the central pipe, a part of the melamine emerging at the top from the central pipe flows downwards in the annular space between the central pipe and reactor wall and the remainder is expelled for further work-up, the off-gases are expelled at the top of the reactor.

DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing, wherein:

FIG. 3b is an end cross-sectional view of the reactor of FIG. 3a.

DETAILED DESCRIPTION

Figure 1:
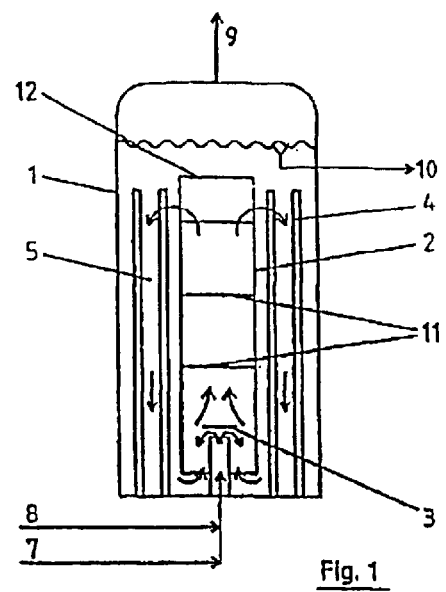
FIG. 1 is a side schematic view of a reaction according to the invention.

To carry out the process according to the invention, urea, which preferably arrives as ammonia-saturated urea melt from a urea scrubber, having a temperature of approximately 135–250° C. is introduced into the melamine reactor from below. Together with the urea, $NH_3$ is optionally introduced into the reactor from below. The molar ratio of the $NH_3$ optionally fed to the melamine reactor to the urea fed is approximately 0–10 mol, preferably approximately 0–5 mol, more preferably approximately 0–2 mol of $NH_3$/mol of urea. The pressure in the melamine reactor, depending on the chosen temperature range, ranges from approximately 50–350 bar, preferably from approximately 80–250 bar.

The temperature in the melamine reactor, depending on the chosen pressure range, ranges from approximately 320–450° C., preferably from approximately 320–400° C., more preferably from approximately 330–380° C.

The melamine reactor is a tank reactor having a vertical central pipe. The urea melt introduced into the central pipe from below and the optionally introduced $NH_3$ preferably flow against a distribution plate installed in the lower part of the central pipe and then further either past the distribution plate or through openings or nozzles which are arranged in a retaining device, for example a retaining plate for the attachment of the distribution plate, on the inlet pipe for urea and $NH_3$, through the distribution plate in the direction of the central pipe. The reactants mix in the interior of the central pipe with the melamine melt circulating in the reactor and likewise flowing into the central pipe from below.

As a result of the intensive mixing of the cool urea melt with the hot, circulating melamine melt in the central pipe, warming of the reactants occurs, and the urea pyrolyses over the height of the reactor to give melamine and off-gas, mainly containing $NH_3$ and $CO_2$. Since the formation of melamine is endothermic, the amount of the melamine circulating in the reactor must be so large that, as a result of the lowering of the temperature of the melamine during the mixing of the reactants and during the pyrolysis of the urea, the danger of solidification of the melamine does not exist.

The desired temperature profile in the reactor can be established by means of the amount of urea introduced, the temperature of the salt melt and the direction of circulation of the salt melt in the double-jacket pipes.

In addition, it is possible to attach, at the bottom of the reactor or in the central pipe itself, fittings, distribution plates or flow guide plates or the like, which make possible a comparative moderation of the flow in the re-routing of the melamine melt from the annular space into the central pipe, a better distribution of the melt flows and the comparative moderation of the bubbles within the central pipe, and also a better separation between melamine melt and off-gas on emergence from the central pipe and at the top of the reactor.

In the upper part of the reactor, the separation between off-gas and liquid melamine takes place. The melamine melt can emerge there both at the upper end of the central pipe and additionally through side openings in the central pipe into the annular space between the central pipe and reactor inner wall.

A part of the melamine flows downward in this annular space, while the remaining melamine melt is expelled from the reactor via an overflow for further work-up. The off-gases are continuously removed at the top of the reactor, preferably in the direction of the urea scrubber. Advantageously, in the region of the separation between off-gas and liquid melamine, baffles or gratings are arranged as a calming zone and for the improvement of the separation action.

In the annular region between the central pipe and the reactor wall are usually situated vertical heating pipes that aid in providing to the reactor the amount of heat necessary for the endothermic reaction. A part of the melamine melt overflowing from the central pipe moves downwards in the annular space on account of the higher density and mixes again with introduced urea in the lower central pipe region, which brings about an internal circulation in the reactor.

The remaining melamine, which is continuously discharged via an overflow at the top of the reactor, is worked up in any desired manner and solidified. This can be carried out, for example, by releasing the pressure of the melamine saturated with ammonia at a temperature which lies barely above its pressure-dependent melting point, by solidification in a fluidized bed or by quenching with water, with liquid or gaseous ammonia or by sublimation and subsequent desublimation from the gas phase.

A further aspect of the invention is a reactor for the production of melamine by pyrolysis of urea, comprising a vertical reactor body having a central pipe, feed lines for urea and optionally $NH_3$ attached in the lower part of the reactor, drain lines for the melamine formed and for the off-gases containing $NH_3$ and $CO_2$ attached in the upper part of the reactor, heating appliances and measuring and control appliances, in particular for temperature, pressure, flow quantities and height level of the melt, characterized in that one or more outlet openings for the supply of urea melt and optionally $NH_3$ are arranged within the central pipe.

In the lower part of the central pipe, a distribution plate for the distribution of the inflowing urea and of the optionally introduced $NH_3$ is preferably installed. The distribution plate can either be designed as a flat plate, or alternatively, for better distribution of the upwardly flowing urea stream and of the likewise upwardly flowing melamine stream, have any desired geometrical shapes, such as, for example, the shape of a pyramid, of a half-dish or preferably the shape of a cone.

It is particularly advantageous if the gap between the distribution plate (3) and the outlet opening of the inlet pipe for the urea melt, and optionally $NH_3$, is as small as possible, for example an annular gap of about 3–13 mm cross-section or openings or nozzles which are arranged in a retaining device, for example a retaining plate for the attachment of the distribution plate to the inlet pipe for urea and optionally $NH_3$. The openings or nozzles can have any desired geometrical shape and are, for example, circular, annular or in the shape of an annular gap. The openings or nozzles are dimensioned such that the emergence rate at the openings or nozzles is about 0.2–10 m/sec, preferably about 1–5 m/sec, more preferably about 0.5–1 m/sec, so that the reactants in the melamine are finely divided. With this arrangement, a higher emergence rate for urea, and optionally $NH_3$, is achieved, which makes possible a better, more intensive and even more homogeneous mixing of the reactants with the outwardly flowing melamine melt. After the emergence from the inlet pipe, the urea stream is preferably diverted in the direction of the central pipe, such that it flows in the same flow direction as the melamine.

The flowing-in of the melamine melt circulating in the reactor from the annular space between the reactor wall and central pipe into the mixing zone with the urea melt, and the optionally introduced $NH_3$, can be made possible, for example, by side openings in the lower region of the central pipe.

Figure 2:
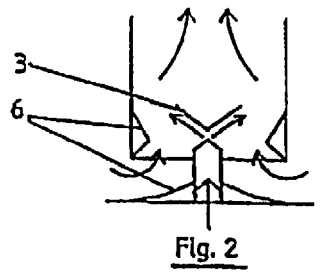
FIG. 2 is a side view of a section of a reactor according to the invention with a cone-shaped distribution plate and flow guide plates.
Figure 3A:
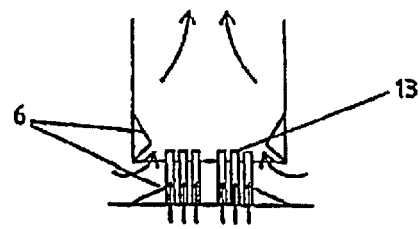
FIG. 3a is a side view of an alternate reactor according to the invention show introduction of a urea melt.
Figure 3B:
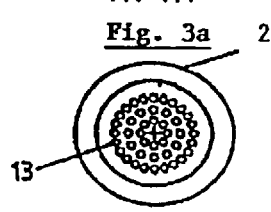
Figure 4:
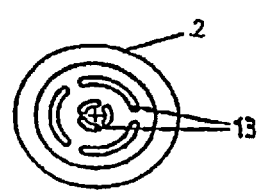
FIG. 4 is a cross-sectional view of an alternative reactor according to the invention showing introduction of urea via annular gaps.

One possible embodiment of the reactor having a flat distribution plate in the central pipe is shown schematically in FIG. 1. FIG. 2 shows a preferred embodiment of the distribution plate in the form of a cone and the incorporation of flow guide plates. FIGS. 3a and 3b show, in the upper part, the introduction of the urea melt by means of nozzles into the interior of the central pipe and in the lower part a cross-section, FIG. 4 shows the introduction of urea via annular gaps in the cross-section.

In FIGS. 1 to 4, the following reference numerals are used: (1) melamine reactor, (2) central pipe, (3) distribution plate, (4) heating pipe, (5) annular space, (6) flow guide plates, (7) supplied urea melt, (8) $NH_3$ gas, (9) off-gases, (10) melamine melt for further work-up, (11) fittings, (12) baffle, and (13) nozzle or annular gap.

The reactor comprises a corrosion-resistant material or is lined with corrosion-resistant material, for example titanium.

It is possible to attach, at the reactor bottom, in the central pipe and/or in the separating zone at the top of the reactor, fittings, distribution plates, flow guide plates or the like, which make possible a comparative moderation of the flow in the redirection of the melamine melt from the annular space into the central pipe, a better mixing of urea and melamine melt, a comparative moderation of the bubble size within the central pipe and on emergence from the central pipe, and a better separation between melamine melt and off-gas at the top of the reactor.

The vertical heating pipes (4), through which the heat necessary for the reaction is provided, are preferably double-jacket pipes in which a salt melt circulates. Here, the supply of the salt melt can be carried out either via the inner pipe cross-section and the discharge via the outer pipe jacket or in the reverse flow direction.

As a result of the mixing and reaction of the reactants within the central pipe, their corroding action comes to bear to a much lesser extent. For example, in a melamine reactor according to the present invention, such as shown schematically in FIG. 1, the decrease in the pipe wall thickness of those heating pipes (4) which lie next to the central pipe (2) is approximately 0.1 mm/year at a capacity of 2.5 t of melamine/h. In comparison, the reduction in the pipe wall thickness with the same high throughputs, but with mixing of the reactants outside the central pipe (2), is up to approximately 0.9 mm/year.

The melamine melt circulating in the reactor serves as a heat-transfer medium for the urea melt introduced into the reactor. Here, an overall decreasing temperature profile is established corresponding to the proceeding urea pyrolysis reaction over the height of the central pipe, i.e. in the vicinity of the melamine overflow from the reactor a lower temperature prevails than at the reactor bottom. The melamine outlet temperature from the reactor is therefore lower than in most melamine processes. It preferably ranges from 330 to 380° C., more preferably from 340 to 370° C. A particular advantage of the reverse flow direction is the low outlet temperature of the melamine melt from the synthesis reactor, which can only thus be run at a lower temperature than in the previously known processes. The melamine synthesis reactor acts in the upper part as a precondenser. Thus the precondensed melamine melt separated from the off-gases arrives even from the start with a lower by-product content for the next working-up steps.

Moreover, as a result of the clean liquid flow—as opposed to a two-phase flow with reversed direction of circulation of the melamine melt—a lowering of the pressure loss in the annular space between the salt melt pipes, and thus an increase in the amount of circulation in the reactor, is achieved. The heat transfer from the salt melt to the melamine melt is thereby improved.

In addition, the possibility exists with fittings in the central pipe of influencing the flow and the bubble size and distribution of the outwardly flowing reaction mixture by means of which a further improvement in the substance and heat transfer can be achieved.

What is claimed is:

1. A process for the production of melamine by pyrolysis of urea in a high-pressure reactor having a vertical central pipe with formation of a melamine melt, comprising:

mixing melamine melt circulating in the reactor in the lower region of the reactor with a urea melt introduced into the reactor from below and optionally with introduced $NH_3$ to form a reaction mixture comprising melamine, $NH_3$, $CO_2$ and optionally reaction intermediates, wherein the reaction mixture flows upwards from below in the central pipe and emerges from the upper part of the central pipe;

separating melamine and off-gas at the top of the reactor above the central pipe, wherein part of the melamine emerging above from the central pipe flows downwards in an annular space between the central pipe and reactor wall and the remainder is expelled for further work-up; and continuously expelling the off-gases at the top of the reactor.

2. A process according to claim 1, wherein the urea melt and optionally the $NH_3$ are introduced into the central pipe from below.

3. A process according to claim 1, wherein the temperature of the melamine melt at the upper end of the central pipe is lower than the temperature of the melamine melt at the lower end.

4. A process according to claim 1, wherein the urea melt and optionally $NH_3$ introduced into the central pipe flow against a distribution plate in the lower part of the central pipe.

5. A process according to claim 1, wherein the melamine melt circulating in the reactor enters into the central pipe through side openings arranged in the lower part of the central pipe, and flows upward in the central pipe and downward in the annular space between the central pipe and reactor wall.

6. A process according to claim 1, wherein the reaction mixture consists essentially of $NH_3$, $CO_2$ and optionally reaction intermediates.

* * * * *